(12) United States Patent
Petek et al.

(10) Patent No.: US 8,085,406 B2
(45) Date of Patent: Dec. 27, 2011

(54) ULTRAFAST MICROSCOPY OF SURFACE ELECTROMAGNETIC FIELDS

(75) Inventors: Hrvoje Petek, Pittsburg, PA (US); Atsushi Kubo, Ibaraki (JP); Nikolaus Johannes Pontius, Berlin (DE)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 419 days.

(21) Appl. No.: 12/199,427

(22) Filed: Aug. 27, 2008

(65) Prior Publication Data

US 2009/0066963 A1    Mar. 12, 2009

Related U.S. Application Data

(60) Provisional application No. 60/969,353, filed on Aug. 31, 2007.

(51) Int. Cl.
*G01B 9/02* (2006.01)
(52) U.S. Cl. ........................................ 356/450
(58) Field of Classification Search ................... 356/450
See application file for complete search history.

(56) References Cited

OTHER PUBLICATIONS

Atsushi Kubo, Ken Onda, Hrvoje Petek, Zhijun Sun, Yun Suk Jung, and Hong Koo Kim, "Imaging of localized silver plasmon dynamics with sub-fs time and nano-meter spatial resolution," in Ultrafast Phenomena XIV. T. Kobayashi, (2005) pp. 645-649, T. Okada, T. Kobayashi, K. Nelson, and S. De Silvestri eds., Springer-Verlag, Berlin (invited talk and proceedings).
A. Kubo, K. Onda, H. Petek, Z. Sun, Y.-S. Jung, and H.-K. Kim, "Femtosecond imaging of surface plasmon dynamics in a nano-structured silver film," (2005), 1123-1127, Nano Lett. 5.
A. Kubo, K. Onda, H. Petek, Z. Sun, Y.-S. Jung, and H.-K. Kim, "Femtosecond imaging of surface plasmon dynamics," (2005), 3-4, SPIE Nanotechnology e-newsletter, 8.
Atsushi Kubo, Yun Suk Jung, Hong Koo Kim and Hrvoje Petek, J. Phys. B: "Femtosecond microscopy of localized and propagating surface plasmons in silver gratings," (2007), S259-S272, Journal of Physics B: Atomic, Molecular and Optical Physics, United Kingdom.
Atsushi Kubo, Niko Pontius, and Hrvoje Petek, "Femtosecond Microscopy of Surface Plasmon Polariton Wave Packet Evolution at the Silver/Vacuum Interface," (2007), 470-475, Nano Lett. 5.

*Primary Examiner* — Hwa Lee
(74) *Attorney, Agent, or Firm* — Kegler, Brown, Hil. & Ritter; James J. Pingor (57) ABSTRACT

System(s) and method(s) to probe electromagnetic fields at the surface of a solid-state material are provided. The technique combines ultrafast (e.g., less than 10 fs) optical excitation and electron microscopy to generate electronic excitations and image the ensuing electromagnetic fields with nanometer-scale spatial resolution and femtosecond time-scale resolution. In addition, time-of-flight energy analysis facilitates imaging of relaxation a generated electronic excitation. The dynamics of the electromagnetic fields can be probed interferometrically through generation of multi-frame imaging, with inter-frame frequency of the order of a few hundreds of attoseconds, of interference patterns among an electric field associated with an excitation in a sample or device and the electromagnetic field of a probe pulse coherent with an excitation pulse. Quality assurance of nanoscopic devices based on plasmonic, photonic, electronic, spintronic operation can be analyzed with spectroscopy provided in the subject innovation.

17 Claims, 8 Drawing Sheets

ULTRAFAST MICROSCOPY OF SURFACE ELECTROMAGNETIC FIELDS

CROSS REFERENCE TO RELATED APPLICATIONS

This application claims the benefit of U.S. Provisional Application Ser. No. 60/969,353 filed on Aug. 31, 2007, entitled "ULTRAFAST MICROSCOPY OF SURFACE ELECTROMAGNETIC FIELDS." The entirety of this provisional application is incorporated herein by reference.

NOTICE ON GOVERNMENT FUNDING

This invention was made with government support under CHE-0507147, DMR-0116034, EECS-0403865 awarded by the National Science Foundation. The government has certain rights in the invention.

TECHNICAL FIELD

This innovation relates to ultrafast time-resolved optical spectroscopy and space-resolved electron microscopy of solid state materials. More particularly, the innovation is directed to time-resolved microscopy.

BACKGROUND

As market forces continue to push the limits of efficiency, capacity, and usability of electronic devices, nanoelectronics emerge as a possible response. In particular, nanoscopic devices have been designed and proposed as new paradigms of computer building blocks, optoelectronic switches, optical detectors, biological labeling, energy conversion, storage media, smart coatings, sensors, etc. Common to these proposals is the fact that excess carriers (e.g., electrons, or holes) are typically responsible for much of the devices' functionality. In addition, in many proposed applications, the devices are probed and manipulated with light, as such a probe is contactless and tends to preserve device integrity, and is faster than conventional electronics.

Light interacting with nanostructured metals and (electron- or hole-doped) semiconductors and semimetals can interact with excess electrons present in the material to excite collective electronic charge-density excitations (e.g., surface and bulk plasmons, magnons in magnetic metals and magnetic doped semiconductors, electromagnetic field induced charge redistribution in quantum dots . . . ). Such excitations are non-trivial since they can be affected by quantum confinement effects and surface effects, in addition to many-body effects which tend to be enhanced upon confinement. Moreover, it should be noted that the excitations are quantum mechanical entities, and as such can exhibit both particle and wave nature. Probing and monitoring these electronic excitations, both in real-space and time-domain, poses a challenge to commonplace techniques such as (i) far-field optical microscopy, which is limited by diffraction to resolution of one-half of the optical wavelength (e.g., above 100 nm), (ii) near-field optical microscopy, which has a very low data acquisition rate, and (iii) electron microscopy, which is typically limited by low-intensity incoherent electron sources to video update rates (e.g. nearly 60 Hz).

SUMMARY

The following presents a simplified summary of the specification in order to provide a basic understanding of some aspects of the specification. This summary is not an extensive overview of the specification. It is intended to neither identify key or critical elements of the specification nor delineate the scope of the specification. Its sole purpose is to present some concepts of the specification in a simplified form as a prelude to the more detailed description that is presented later.

Disclosed herein is an instrument platform that combines the spatial resolution of electron microscopy and the temporal resolution of ultra-fast femtosecond laser spectroscopy into an interferometric time-resolved photoelectron emission microscope. Combination of spatial and temporal resolution spectroscopy affords 4-dimensional imaging of electromagnetic fields and excitations in probed materials. In an aspect, imaging proceeds by detecting with a photoemission electron microscope the nonlinear multi-photon photoemission of electrons excited with time-correlated femtosecond laser pulses in the visible and near ultraviolet regime. In addition, by scanning the delay between identical pump and probe laser pulses with interferometric (sub optical period) resolution, the evolution of surface electromagnetic fields can be captured. Moreover, by performing spatially resolved time-of-flight energy analysis of photoemitted electrons, images of electron relaxation at solid surfaces can be developed. In addition, by performing spatially resolved time-of-flight energy analysis of photoemitted electrons, 4-dimensional (e.g., position on a surface, time, and energy) images of electron energy and momentum relaxation at solid surfaces can be generated.

It should be appreciated that the microscopy instrument platform and technique(s) described herein can probe disparate metallic materials with complex nanostructures, including those that display defects; photonic and plasmonic materials; metamaterial-based devices; as well as nanostructured materials employed in development and optimization of novel electronic and optical devices. Furthermore, it can also be possible to employ the technique disclosed hereinafter to control the propagation, dephasing, diffraction, interference, focusing, and localization of light with sub-wavelength resolution. Further yet, the microscopy instrument platform can be utilized to (i) image electric fields associated with electronic excitation in molecules of biological interest, and molecules that can make part of molecular electronic devices; (ii) probe quantum mechanical properties of carrier in a sample or device; (iii) concentrate light on the nanometer scale; (iv) observe how concentrated electromagnetic fields can drive nonlinear and nonthermal phenomena in solids, such as phenomena that occurs in optically assisted magnetic recording; (v) create localized phase changes in a material; and (vi) provide the means for local probing of a material's properties.

In another aspect, microscopy instrument platform and technique(s) described herein can be employed for quality assurance of solid-state devices. Device structural and functional integrity can be tested, at least in part, through the various space-, time-, and energy-resolve microscopy capabilities of microscopy instrument platform disclosed in the subject innovation.

The following description, the annexed drawings and appendices set forth, in detail, certain illustrative aspects of the innovation. These aspects are indicative, however, of but a few of the various ways in which the principles of the innovation may be employed and the subject innovation is intended to include all such aspects and their equivalents. Other objects, advantages and novel features of the innovation will become apparent from the following detailed description of the innovation when considered in conjunction with the drawings.

DETAILED DESCRIPTION

The subject matter is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present innovation.

As used in this application, the terms "component," "system," "platform," and the like are intended to refer to an entity that is either hardware, a combination of hardware and software, software, or software in execution. Hardware components can be composed of various components that provide at least part of the functionality of the hardware component. In addition, functionality of hardware components can be provided at least in part by a processor that executes a software component that resided within a hardware component. For example, a component may be, but is not limited to being, a process running on a processor, a processor, an object, an executable, a thread of execution, a program, a computer, a electromechanical appliance, and/or a mechanical appliance. Also, these components can execute from various computer readable media having various data structures and code instructions stored thereon. Execution is generally accomplished via a processor that executes the components, or code instructions associated therewith, stored in the computer readable media. Components can be networked (e.g., through a local system of via a wide area network) and may communicate via local and/or remote processes.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

A novel instrument platform and technique(s) provide space-, time-, and energy-resolved imaging of electromagnetic fields associated with electronic excitations, and relaxation of electronic excitations in surfaces of condensed matter like nanostructured metallic, semi-metallic, and semiconductor solids. The subject innovation exploits ultra-high spatial resolution attained in electron microscopy, the fine time-resolution of ultrafast femtosecond laser spectroscopy, and energy resolution of time-of-flight energy analysis. As described in greater detail below, the instrument platform can be embodied in an interferometric time-resolved photoelectron emission microscope (ITR-PEEM) with time-of-flight energy analysis detection capabilities.

Figure 1:
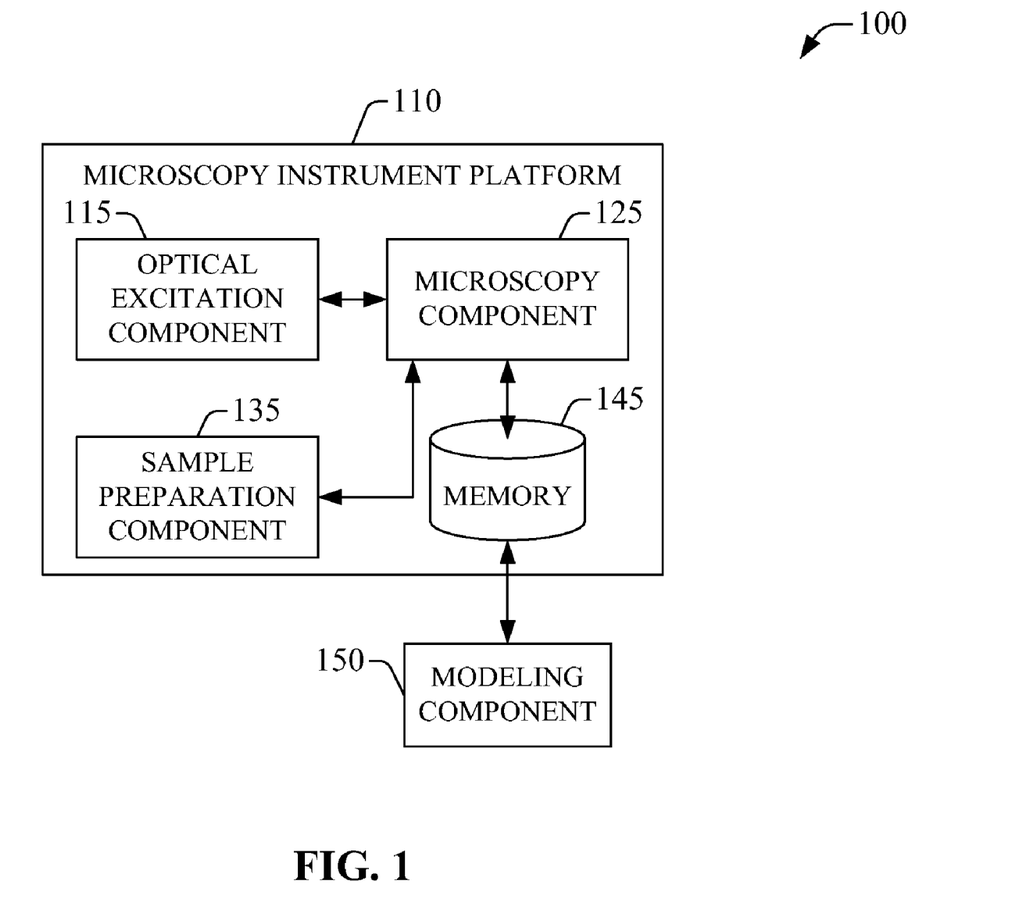
FIG. 1 is a block diagram of a microscopy instrument platform that facilitates probing an electronic excitation in accordance with aspects of the subject innovation.

FIG. 1 illustrates in a block diagram an example system 100 that facilitates to probe an electronic excitation in a solid state material (e.g., a nanostructured metal, semi-metal, or doped, like p-type, n-type semiconducting solid) or molecules of biological interest (e.g., DNA strands, RNA strands). In system 100, a microscopy instrument platform 110 can generate and probe an electronic excitation and an electromagnetic field associated therewith. In addition, microscopy instrument platform 110 can facilitate detection of relaxation of a generated electronic excitation. To the accomplishment of the latter, optical excitation component 115 generates laser pulses that are utilized to produce (or "pump") an electronic excitation in a sample (e.g., a nanostructured solid surface, like an orderly or randomly textured surface with texturing features with typical length scale(s) of less than 10 nm, which can result in quantum confined electronic states; or a solid-state device with nanostructure features), and subsequently probe such excitation; the probing can be done interferometrically, wherein a probe laser pulse interferes with an electromagnetic field associated with the generated electronic excitation. Microscopy component 125 can collect data related to the excitation through detection, or spectroscopy, photoemitted electrons (e.g., nonlinear multi-photon photoelectron emission or microscopy) generated as a result of the probing of the sample or device.

Through optical excitation component 115 and microscopy component 125, microscopy instrument platform 110 can afford imaging the spatial distribution of electromagnetic fields with sub-wavelength spatial resolution of less than 50 nm, the electromagnetic fields associated with an electronic excitation (e.g., surface plasmon, or surface plasmon polariton) in a surface of a conductor or semiconductor. Likewise, microscopy instrument platform 110 can afford time-resolved experiments, with a resolution of less than 10 fs. Dynamics of an electronic excitation can be monitored through multi-frame imaging, or movies, of electromagnetic fields associated with the electronic excitation, or spatial distribution of excited electronic density. Movies can be recorded interferometrically as described in the subject specification. In addition, or alternatively, movies can be recorded through combination of the pump and probe pulses such that phase is not well defined, because of at least their manner of scanning, overlapping, or generating. Furthermore, microscopy instrument platform 110 can afford spatially resolved time-of-flight energy analysis of photoemitted electrons, which can provide data on relaxation of electronic excitation, populations at solid surfaces, e.g., excited electron in the surface of a doped semiconductor. From the energy of a photoemitted electron we can get the energy of a transiently excited electron in a solid-state material. The foregoing aspects, or capabilities, of microscopy instrument platform 110, can provide 4-dimensional imaging of electromagnetic fields associated with electronic excitations and relaxation thereof at a solid surface; the four-dimensional space spanned by a two-dimensional space of position on the probed surface, a time of an excitation and an energy of an excited carrier (e.g., electron or hole).

The combination of components 115 and 125 to attain the imaging and monitoring of the time-dependent behavior of an electronic excitation is herein termed interferometric time-resolved photoemission electron microscopy (ITR-PEEM). It should be appreciated that the ITR-PEEM based microscopy instrument platform 110 can also reach spatial resolution that is limited by the wavelength of photoelectrons, which can be less than 1 nm for photoelectrons with typical energies of nearly 1 eV, and temporal resolution below 1 fs which is limited by a laser pulse width of a light source employed for optical excitation.

Sample preparation component 135 is utilized to produce nanostructured metallic or semiconducting materials (e.g. coating a glass or mica substrate with a metal (e.g., Ag, Pt, Au) thin film, a metal slab with thickness of 400 nm and grating with periods that range from about 800 nm to 1.8 μm, or a metal slab nearly 80 nm thick with sporadic extended line defects due to cleavage, and so on). Samples can also be nanoscopic devices of various types such as phononic (e.g., suspended micro-electromechanical machines for heat transport), plasmonic, photonic (e.g., metal thin slabs with patterned nm-sized perforation or fillings; molecular electronic (e.g., strands of DNA or substantially simpler molecules attached to metal leads); spintronic (e.g., semiconducting nanowire with excess electrons or holes, or molecules attached to magnetic leads); quantum dot-based electronic (e.g., lithographically gated quantum dots on electron-doped semiconductors, like quasi-two-dimensional electron gases on GaAs; a metal nanoparticle or arrays of metal nanoparticles); electronic based on low-dimensional carbon films (e.g., graphene sheets or carbon nanotube wires; etc. The various types of devices typically determined, at least in part, by the nature of carriers (e.g., electron, hole), quasi-particle (e.g., photon, phonon) or degrees of freedom (e.g., charge, spin) exploited for functionality.

Additionally, sample preparation component 135 can include low-energy electron diffraction (LEED) optics; ion sputtering gun, electron gun, for generation of lithographic patterns on a surface; electron beam (e-beam) evaporator to coat various insulating, dielectric or semiconducting substrates with metal films or nanostrutures; alkali atom getter source to control the work function of the sample; crystal thickness monitor to control deposition processes for preparation of samples or devices. It should be appreciated that sample preparation component 135 can facilitate coating (e.g. coating with silica) of materials of biological interest such as DNA strands, amino acid and proteins to prevent degradation and to mimic an aqueous environment in which such materials operate. In an aspect of the subject innovation, coating can be performed through multiple sources and in a spatially inhomogeneous manner in order to facilitate combinatorial discovery of electronic solid-state materials with specific target electronic properties. Spatially varying electronic properties of such inhomogeneous materials can provide spatial and temporal contrast, which can be recorded via microscopy component 125. Sample preparation component 135 can also include a load-lock chamber for rapid insertion of a sample or device into microscopy component 125 (e.g., insertion into a vacuum chamber) or exchange within disparate parts thereof (e.g., exchange into a microscope sample stage. Even though illustrated as external to microscopy component 125, it should be further appreciated that sample preparation component 135 can reside within microscopy component 125.

Memory 145 can retain measurements and associated data structures generated by microscopy component 125. Additionally, memory 145 can store code instructions for automated or agent-driven (e.g., operator, engineer) operation of substantially any component that is part of the microscopy instrument platform 110.

In addition, a modeling component 150 can be functionally coupled to microscopy instrument platform 110 to afford process and analysis of data related to spectroscopy of an electronic excitation, the data generated through at least one of space-resolved photoemission spectroscopy, time-resolved pump-and-probe interference spectroscopy, or energy-resolved time-of flight analysis of photoemitted electrons. It is noted that modeling component 150 can be employed to simulate measured data generated in accordance with aspects described herein, and retained in memory 145.

Modeling component 150 can contain (e.g., in a memory (not shown)) a number of models or algorithms that can predict optical and electronic properties (e.g., light absorption/emission spectra, ellipsometry spectra, frequency-dependent dielectric constants, energy spectrum of electronic excitations, electronic energy structure, quasi-particle relaxation rate(s)) of a sample or device being probed with ITR-PEEM, as well as electromagnetic fields generated by a particular electronic excitation that is accessed by microscopy instrument platform 110. Moreover, modeling component 150 can comprise a design simulation package (e.g., a suite of various computer program products, and related code instructions) that allows simulation of the ITR-PEEM spectroscopy response of a set of idealized devices in order to find a solid-state device or sample with a set of desired properties (e.g., specific plasmon resonance energy, dephasing times, excitation lifetimes . . . ). Such simulation package can also include a capability to simulate electronic structure of solid state device(s) or sample(s), this capability can facilitate optimization of the coupling structures for nanoscale optical elements, and propagation and focusing of electromagnetic fields in space (e.g., a region in a device) and time (e.g., a specific instant during operation of a device). Furthermore, modeling component 150 can also include simulation packages, or computational tools, to facilitate materials combinatorial design and discovery. Modeling component 150 can include a processor (not shown) that can execute, at least in part, code instructions associated with such models/algorithms stored in the memory (not shown).

Spectroscopy instrument platform 110 can be utilized in at least the following applications: (i) to image electric fields associated with electronic excitation in molecules of biological interest, and molecules that can make part of molecular electronic devices; (ii) to concentrate light on the nanometer scale; (iii) to observe how concentrated electromagnetic fields can drive nonlinear and nonthermal phenomena in solids, such as phenomena that occurs in optically assisted magnetic recording; (iv) to create localized phase changes in a material; (v) to provide the means for local probing of a device's properties; and (vi) to image the electronic properties of spatially inhomogeneous materials such as those produced by spatially varying, multi-source material deposition, or through antibody-antigen interaction.

Next, aspects of example optical excitation component 115 and microscopy component 125 are discussed in greater detail in connection with FIGS. 2A-2B.

Figure 2A:
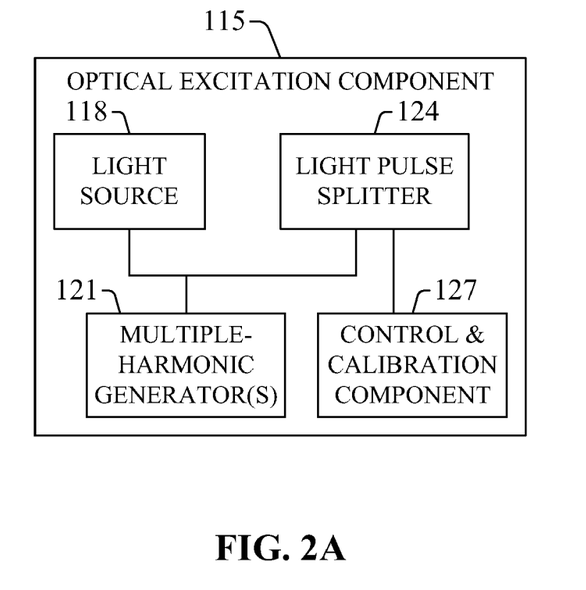
FIGS. 2A-2B are block diagrams of example optical excitation component and microscopy component that are part of microscopy instrument platform disclosed herein.

FIG. 2A illustrates an example embodiment of optical excitation component 115. A light source 115 can include a laser oscillator to generate ultrafast (e.g., of the order of 10 fs) laser pulses with wavelengths that range from the visible to ultra-violet (UV) portion of the electromagnetic radiation spectrum. Light source can generate polarized light (e.g., linearly P-polarized or S-polarized light with respect to the optical plane defined by the reflection of light from a surface of a sample or device. Average power of generated laser pulses typically ranges from 90-100 mW, and laser pulses can form a train of pulses with repetition frequencies of nearly 90 MHZ. In an aspect of the subject innovation, the laser oscillator is a custom-engineered Ti:sapphire laser oscillator that can generate laser pulses with duration of less than 10 fs (e.g., 8 fs pulse) and a wavelength of 780 nm (hv=1.59 eV) from a negative group-velocity dispersion mirror compensated cavity. Light source 115 can also include an optical dispersion compensation assembly of mirrors (e.g., a set of pairs of dielectric mirrors) to correct for positive dispersion associated with generation and propagation of the femtosecond pulses, and to achieve a substantially minimum pulse duration at a probed sample. In addition, light source 115 can also include substantially any UV light source lamp for excitation of a sample; for instance, unpolarized continuous-wave gas discharge source such as Hg (primary line 254 nm; hv=4.89 eV), Ar, Na, Xe, Ne, Kr, W (primary line $\lambda$=255 nm; hv=4.86 eV) lamps. It should be noted that CW excitation can be employed for coarse imaging or topography determination of a device.

Optical excitation component 115 includes a multiple harmonic generator(s) 121 which can facilitate adjustment of the excitation frequency of laser pulses generated in light source 118. It should be appreciated that disparate multiple harmonic generators can be set-up in disparate stages of an optical path of a laser pulse in order to achieve laser pulses of disparate colors, or frequencies. For example, frequency can be doubled through second harmonic generation based at least in part on an all-reflective frequency doubler that exploits a thin slab (e.g., 80 $\mu$m) of a BBO ($\beta$-$BaB_2O_4$) crystal. In an aspect, laser pulses of $\lambda$=390 nm (hv=3.19 eV; radiation in the UV) with nearly 10 fs duration and nearly 150 mW average power can be achieved with a substantially 20% conversion efficiency from source 8 fs pulses with $\lambda$=780 nm and 90-100 mW average power. Center wavelength of frequency-multiplied pulses can be scanned over a wavelength interval (e.g., 30 nm) about a nominal frequency of a multiplier crystal (e.g., a BBO crystal) via an adjustment of phase matching condition(s) of the multiplier crystal (e.g., BBO).

In addition, optical excitation component 115 also includes a light pulse splitter 124. Once light source 118 generates a pulse train, each pulse in the pulse train, either frequency-multiplied or not, can be split in two substantially identical, phase-locked pulses, which can be employed to excite in pump-probe mode a sample (e.g., a metal grating) or device (e.g., a nanowire-based single-electron transistor). The phase-locked nature of pump-probe pulses that result from division of a source pulse can facilitate coherent probe of electronic excitations and temporal evolution associated therewith, which can afford multi-frame imaging (e.g., a movie generation) of such evolution. The multi-frame imaging is recorded through a scan of a relative delay of pump and probe, and locked to a specific phase of the probe or source pulse. In an aspect of the subject innovation, pulse splitting is accomplished as follows. A source pulse train enters an interferometrically stabilized Mach-Zehnder interferometer (MZI) which creates two collinear replicas of the source pulse. Interferometric scan of the length of one arm of the MZI modulates a mutual delay $\Delta\tau$ among the created replica pulses with an accuracy better than 50 attoseconds (5× $10^{-17}$ s), corresponding, for example, to less than 1/25 of an optical cycle (1.33 fs) of radiation with $\lambda$=400 nm. For multi-frame imaging, $\Delta\tau$ can be in 1/4-cycle steps which can afford recordation of a movie with an interval of 330 as/frame of a dynamics of an excitation (e.g., a surface plasmon, a surface plasmon polariton, a magnon, and so on). In an aspect, for each delay $\Delta\tau$, each image in a multi-frame movie is integrated over several independent pump-probe cycles throughout an exposure time of 10 seconds.

Optical excitation component 115 can also include a control and calibration component 127 that provides an absolute time reference for delay $\Delta\tau$ in the interferometrically split laser pulse.

Figure 2B:
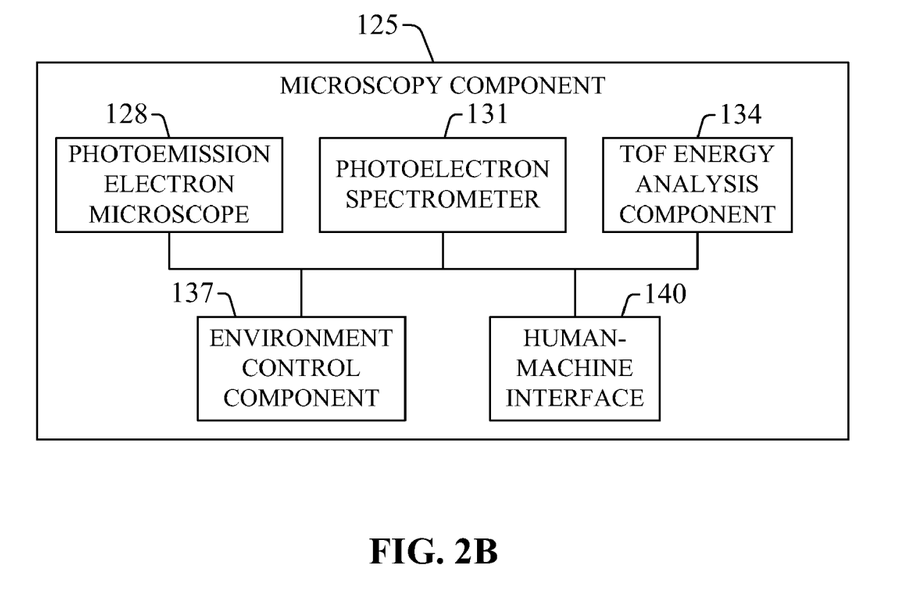

FIG. 2B illustrates an example embodiment of microscopy component 125. This embodiment can include a photoemission electron microscope 128, with associated focus (e.g., a calcium fluoride plano-convex lens that can focus excitation light at 65 degrees from the surface normal of a sample or device, or focus elements for photoemitted electrons) and detection elements. For example, a multichannel intensifier-CCD (charge-coupled device) camera combination, which can provide energy-integrated images. Microscopy component 125 can also include a photoelectron spectrometer (PS) and associated detection components to measure photoelectron energy and momentum. A sample or device to be proved can be located in either the PS or the PEEM chambers. The photoelectrons emitted by one-photon absorption, when light source 118 delivers an optical excitation with sufficient energy to photoemit an electron upon light absorption in a sample or device; or non-linear multi-photon absorption in the sample or device (e.g., a nanostructured metal thin-film on an insulating substrate) can be imaged with the PEEM 128 optics and recorded in data stored in data store 145. It should be appreciated that imagery gathered with photoelectron spectrometer 131 typically relies on linear absorption of light from generally low-intensity optical excitation pulses or CW excitation.

Microscopy component 125 can also include a time-of-flight (TOF) energy analysis component 134. Such analysis of photoemitted electrons in a pump-and-probe spectroscopy experiment as described herein can monitor energy-resolved electronic excitation relaxation in a sample or device, which can provide direct estimates of relaxation times and spatial pathways of specific excitations from data. It should be appreciated that at the very least an advantage of probing excitation relaxation directly is to probe devices in operation and associated microscopic mechanism(s) related to functionality of the devices.

In an aspect of the subject innovation, detection of photoemitted electrons in the photoelectron spectrometer is accomplished through a wire grid spatial-temporal (e.g., (x, y; t)) detector, which affords energy-resolved images, and gated clocking or timing electronic components. Detection resolution of time of arrival of a photoelectron is no less that 100 ps. A clock in the detection circuitry is triggered by a photoemitted electron, which has a specific energy, and the subsequently arriving laser pulse from a pulse train of excitation pulses with a pulse-to-pulse jitter of much less than 100 ps switches off the clock, and a time-of-flight is determined. It should be noted that the clock in time-of-arrival electronics is gated through the variable arrival time of detected photoelectrons with respect to the constant arrival time of the optical excitations (e.g., laser pulses). To probe an electron relaxation time, counts of photoemitted electrons of a specific energy emitted from a well-defined position in a spatial grid of x, and y spatial coordinates, and substantially in resonance with an electronic excitation in a sample or device are accumulated and analyzed as a function of delay time. Evolution of cumulative counts versus $\Delta\tau$ facilitates extraction of a relaxation time for a specific electronic excitation. It should be appreciated that a sample or device exhibits a spectrum of excitation which can occur at discrete energies or otherwise. Through TOF energy analysis component 134 and photoemission electron microscopy, the subject innovation can probe electronic excitation relaxation directly with reference to specific energy and position within the sample.

In addition, or alternatively, in another aspect of the subject innovation, energy analysis can be accomplished by electrostatic methods, especially when a specific instant in a relaxation process and a narrow energy range associated with the electronic relaxation of interest, as opposed to probing an entire accessible (e.g., defined by a detector that is employed) energy spectrum simultaneously. Determination of a specific electronic excitation can be driven through simulations (e.g., conducted via modeling component 150) or experimentation.

In addition, microscopy component 125 can include an environment control component 137 that can facilitate establishing conditions for an operational environment of a device or sample that is probed. For instance, environment control component can vary temperature(s); magnetic and electric field(s); gate voltage(s) and source and drain voltages; and so on. It should be appreciated that magnetic fields can be utilized to switch magnetization of a sample, and are typically applied before a measurement to avoid affecting operation of the ITR-PEEM. It should be further appreciated that environment control component 137 can comprise various active elements that facilitate control of the foregoing external operational parameters and fields. A human-machine interface 140 is included in microscopy component 125 to facilitate operation and maintenance thereof. Operation includes utilization of display interfaces to set experimental conditions (e.g., temperature, magnetic field, selected light source, etc.) and monitor data acquisition.

Figure 3:
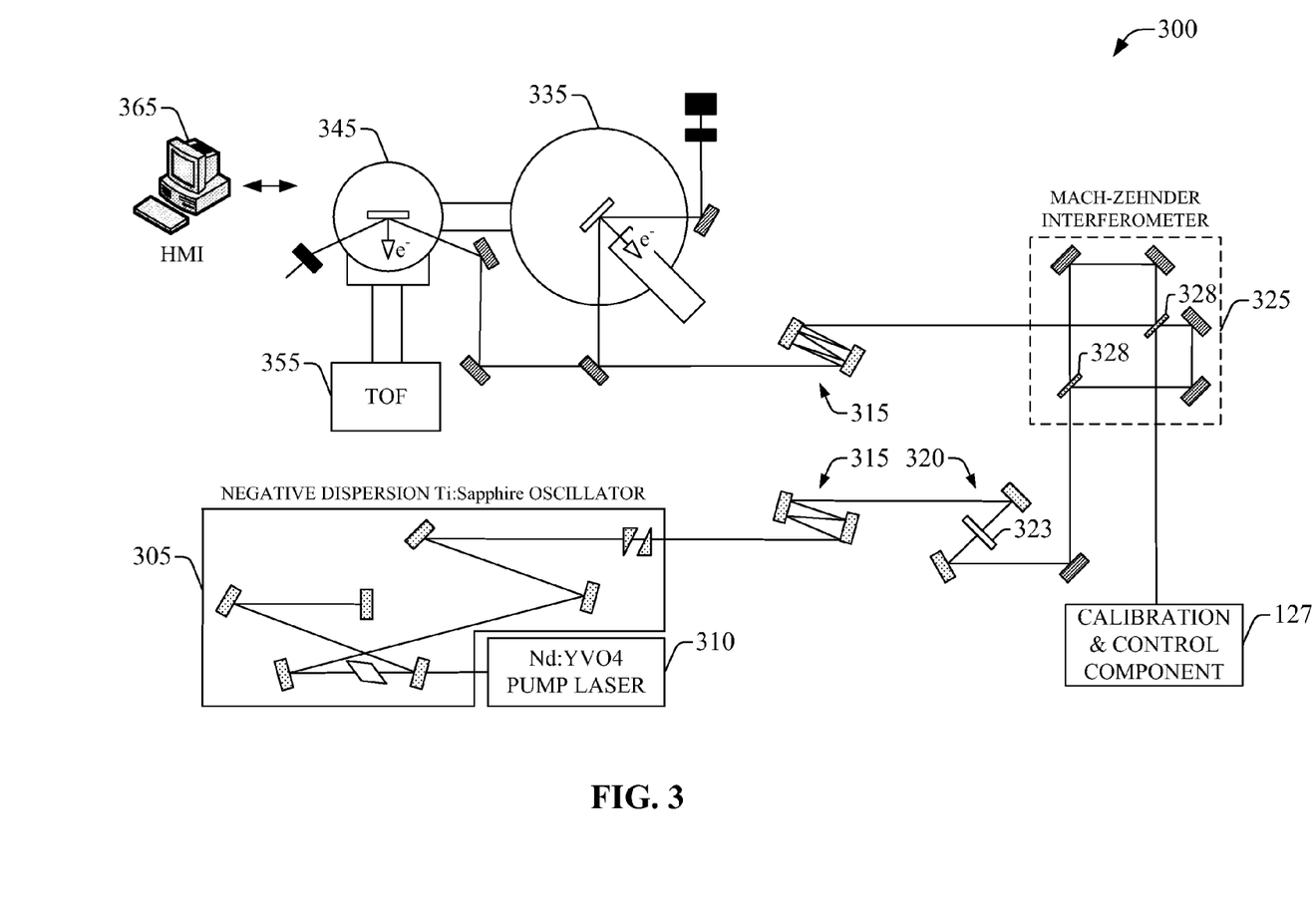
FIG. 3 is a block diagram of an illustrative example realization of a microscopy instrument platform in accordance with aspects disclosed herein.

FIG. 3 is a block diagram 300 of an illustrative example realization of a microscopy instrument platform 110 in accordance with aspects disclosed herein. In diagram 300, light rays are sketched as straight lines. A light source is embodied in a negative dispersion Ti:sapphire oscillator 305 pumped with a Na:YVO4 cw laser 310. The Ti:sapphire oscillator 305 provides a steady train of pulses with a specific repetition rate (e.g., 90 MHz), which is determined and can be varied by the optical path length a pulse traverses within the oscillator. The repetition rate can be reduced by opto-electronic switching of pulses, or it can be increased by splitting single pulses into multiple pulses with a fixed delay. Output of the Ti:sapphire is pulsed and affected by positive group velocity dispersion. To compensate such distortion a pair of negative dispersion chirped mirrors 315 collect the output of Ti:sapphire oscillator 305. After dispersion correction, light is conveyed to a second harmonic generator or frequency doubler 320; a thin (e.g., nearly 80 μm) BBO crystal 323 provides with the double frequency radiation pulse as described hereinbefore. Frequency-doubled pulse enters a Mach-Zehnder interferometer (MZI) 325 and is replicated into two identical, collinear phase-locked pulses. The two pulses can be delayed and the delay is controlled through the optical path within one of the arms of the MZI. Semireflective mirrors 328 in the MZI split the pulses, and make them collinear but delayed after exit of the MZI. It should be noted that in example microscopy instrument platform 110 as illustrated in diagram 300, a second frequency doubler can be deployed within one of the arms of MZI in order to generate pump and probe laser pulses of disparate colors. Generated pulses, of the same color or otherwise, are utilized as pump and probe pulses as described hereinbefore, and prior to exciting a sample or device, pulses are corrected for optical dispersion that may arise from frequency doubling at the second harmonic generator 320 or replication at the MZI 325. Pump and probe laser pulses can excite a sample or device within either a PEEM chamber 335 or a photoelectron spectrometer 345 and associated detection component 375. In an aspect, environment of a sample or device can be controlled (e.g., temperature can be regulated within a 50 K-1500 K interval), and external probe fields (e.g., magnetic, electric) can be applied as well. Photoemitted electrons (illustrated with an open-head arrow) are collected and detected with suitable detection circuitry included within each chamber. In addition, photoemitted electrons can undergo time-of-flight energy analysis, which is facilitated by a time-of-flight component 355 which operates in substantially the same manner as TOF energy analysis component 134, and includes appropriate instrumentation and electronic circuitry that facilitates operation. In diagram 330, a human-machine-interface 365 facilitates operation of the example microscopy instrument platform.

Figure 4:
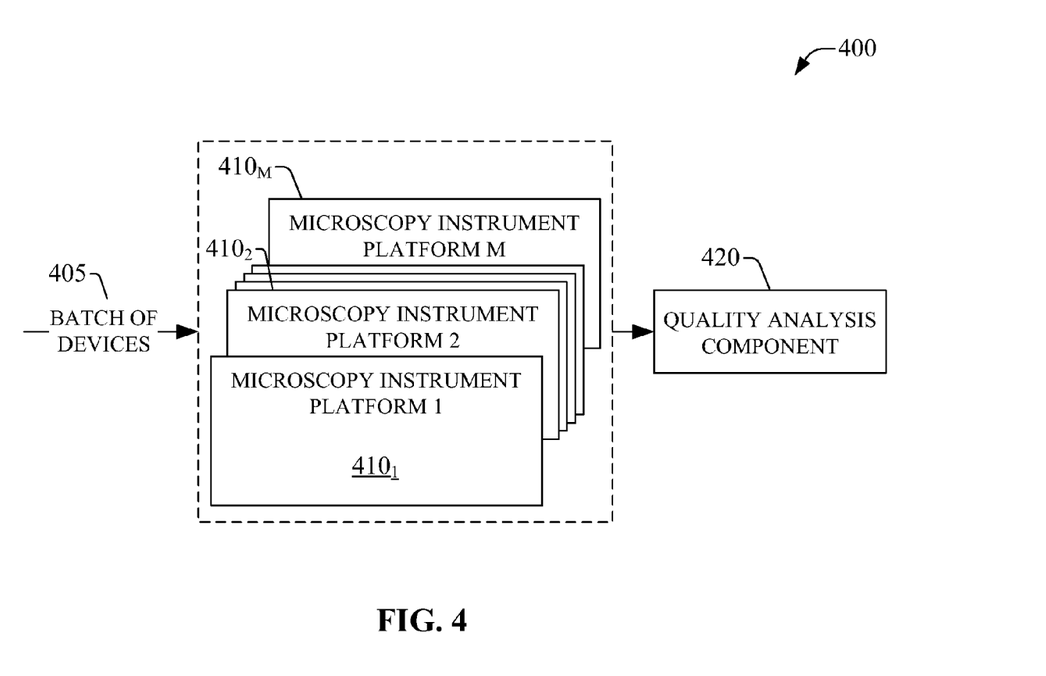
FIG. 4 illustrates a block diagram of an example system that facilitates quality assurance for a batch of devices in accordance with aspects described herein.

FIG. 4 illustrates a block diagram of an example system 400 that facilitates quality assurance (QA) of a batch of devices in accordance with aspects described herein. A batch of devices 405 (e.g., nanoscopic plasmonic devices, quantum-dot based or molecular electronic devices, photonic devices, or spintronic devices) are conveyed to a deployed quality assurance platform that can include M (with M a positive integer) microscopy instrument platform $410_1$-$410_M$. Four-dimensional imagery as afforded through ITR-PEEM experiments described herein can be employed to determine are test device integrity. For example, structural characteristics of surface of device(s) within the batch of devices 405, and to probe for various electronic excitations in several positions in the device(s). Structural characteristics can include presence of defects in operationally critical regions of a device, or sizes of nanoscopic features that provide functionality to the device through determination of electronic structure and spectrum of electronic excitations, such features includes perforations, dielectric inclusions, width of grating elements, size of deposited nanoparticles, diameter of nanowires. It should be appreciated that ultrafast resolution (e.g., less than 1 fs) of time-resolved spectroscopy, and energy resolved time-of-flight energy analysis afforded by microscopy instrument platform(s) $410_1$-$410_M$ can facilitate testing devices in operation to ensure functionality is adequate or device design is warranted.

In addition, a quality analysis component 420 can evaluate spectroscopic data on batch of devices 405 collected by microscopy instrument platform(s) $410_1$-$410_M$. Analysis can determine, for example, whether density of defects in devices is either tolerable or uniform, or both, a desired functionality performance is achieved, or device design alterations are necessary. Quality analysis can include split sampling, wherein spectroscopic data of disparate sets of devices within batch of devices 405 collected from disparate microscopy instrument platforms, e.g., $410_2$ and $410_N$, is compared to corroborate or refute QA findings and recommendations. Quality analysis component 420 can include a memory (not shown) that retains data and code instructions for QA analysis, and a processor (not shown) that can execute such instructions.

In view of example platform(s) and system(s) shown and described above, methodologies that may be implemented in accordance with the disclosed subject matter will be better appreciated with reference to the flowcharts of FIGS. 5-8. While, for purposes of simplicity of explanation, the methodologies are shown and described as a series of blocks, it is to be understood and appreciated that the claimed subject matter is not limited by the number or order of blocks, as some blocks may occur in different orders and/or concurrently with other blocks from what is depicted and described herein. Moreover, not all illustrated blocks may be required to implement the methodologies described hereinafter. It is to be appreciated that the functionality associated with the blocks may be implemented by software, hardware, a combination thereof or any other suitable means (e.g., device, system, process, component). Additionally, it should be further appreciated that the methodologies disclosed hereinafter and throughout this specification are capable of being stored on an article of manufacture to facilitate transporting and transferring such methodologies to various devices. It should be understood and appreciated that a methodology could alternatively be represented as a series of interrelated states or events, such as in a state diagram or interaction diagrams.

Figure 5:
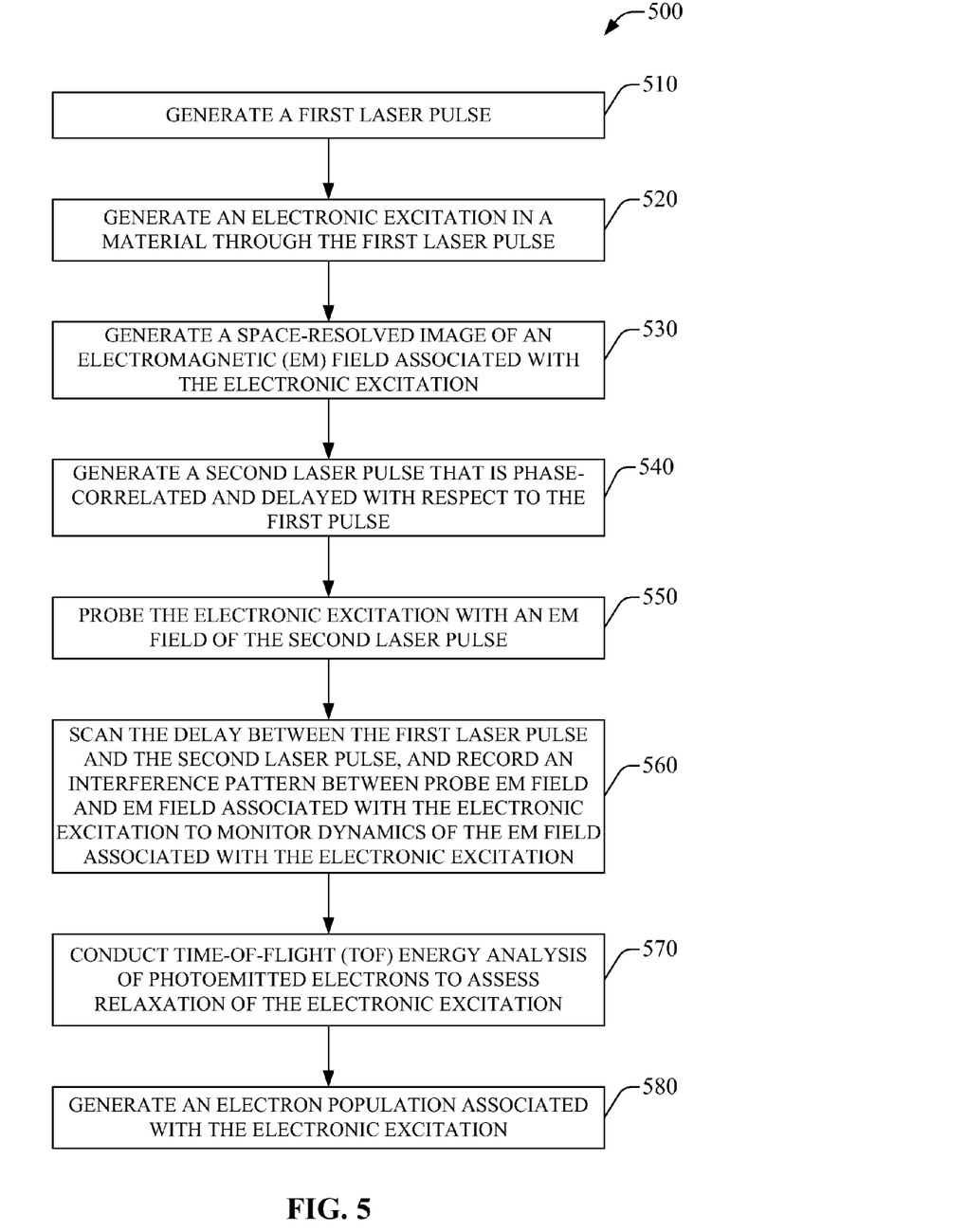
FIG. 5 is a flowchart of an example method for generating spectroscopic data on electronic excitations, and associated electromagnetic fields, resolved in space, time, and energy according to aspects described herein.

FIG. 5 presents a flowchart of an example method 500 for generating spectroscopic data on electronic excitations, and associated electromagnetic fields, resolved in space, time, and energy. At act 510 a first laser pulse is generated. Such generation can be accomplished through light source 118 within optical excitation component 115. In an aspect, generated first laser pulse can have a well-defined polarization. At act 520, an electronic excitation in a material is generated through the first excitation pulse. Generation of an electronic excitation demands employing laser pulses with an adequate photon energy, as excitation energy spectrum depends on the sample or device probed (e.g., electron-doped nanostructered semiconductor, metal, metal-based metamaterial, metal nanoparticles, core-shell nanoparticles, doped colloidal quantum dots passivated with DNA strands, graphene or carbon nanotube structure, and so forth) In an aspect, generating an electronic excitation in a novel device can require input from simulations of possible electronic excitation in the device. In another aspect, cases in which realistic simulations are not feasible or fail to predict the observed spectrum of excitations of the device, complementary experiments may be necessary in order to excite a device with laser pulses of the right energy. At act 530, a space-resolved image of an electromagnetic field associated with the electronic excitation is generated. In an aspect, spatial resolution can be substantially below the wavelength of the laser pulse. Such a field can be employed as a unique signature of the excitation and the properties of a material/device in which the excitation is generated. Such a unique signature can be employed to monitor changes in the material/device, e.g., by monitoring features of the generated electromagnetic field. In an aspect, presence/absence of a specific feature in the amplitude of the electromagnetic field can indicate the presence or absence of a defect in the device. In addition, detected spectroscopic shifts of the excitation energy or the time course, or progression, of the changes in the signal amplitude can be used to monitor presence/absence of defects in the surface of a material.

At act 540, a second laser pulse is generated, the laser pulse is phase-correlated and delayed with respect to the first pulse. In an aspect, the second laser pulse is generated interferometrically in a Mach-Zehnder interferometer, which ensured the second pulse is substantially collinear with the first laser pulse and the phase of the second pulse is locked with the phase of the first laser pulse. Thus, pump excitation and probe through first and second laser pulses, respectively, remains coherent. The coherent nature of pump-and-probe space-, time-, and energy-resolved experiments in accordance with the subject innovation, can afford probing quantum mechanical properties of ground state and excited carriers: For instance, probability distributions, ballistic transport, e.g., through molecular junctions which can be deposited on solid surfaces; interference among carriers, which can dictate mutual dephasing among wave functions of the carriers and thus affect quantum computing via gated quantum dots; and so on. Mutual delays among first and second laser pulses can be determined with a resolution of less, or no more, than 50 attoseconds. Generated pulses can be monochromatic or have disparate frequencies, or color. In an aspect, the first laser pulse can be tuned in wavelength to a specific excitation in a sample or device, in order to enhance the imaging contrast of a specific process. The second pulse of different color can be employed to induce photoemission in accordance with appropriate energy threshold (e.g., work function). Such experimentation with laser pulses of different colors, at least advantageous, for instance, when two photons of the first color are insufficient to induce photoemission in the sample or device. It should be noted that the two laser pulses of disparate colors can be phase correlated if they are different harmonics of the same laser (e.g., attained through multiple harmonic generator(s) 121), or are derived by optical parametric generation (e.g., within the light source 118). Moreover, the excitation pulses can have well-defined phase with respect to the carrier envelope of the laser pulse, allowing measurements to be performed that depend on the absolute phase of the excitation field. In cases the two pulses with disparate colors are not phase-locked, microscopy measurements can sense change(s) in population of excited carriers but not their phase.

At act 550, the electronic excitation is probed with an electromagnetic field of the second laser pulse. At act 560, the delay between the first and second laser pulse is scanned, and an interference pattern among the probe electromagnetic field of the second laser pulse and the electromagnetic field associated with the electronic excitation that was created by the first pulse is recorded, wherein the time-dependence of the recorded interferometric pattern among electromagnetic fields is utilized to monitor dynamics of the electromagnetic field associated with the electronic excitation. In an aspect, multi-frame imaging can be recorded with a delay rate of ¼ of the optical cycle of a 400 nm radiation (330 attoseconds) per frame. It should be appreciated that imaging through interference between the electromagnetic (EM) field associated with the electronic excitation and the electromagnetic radiation field of the second laser pulse can proceed until the EM associated with the electronic excitation dephases with respect to the probe EM field. Dephasing is device dependent and typically is associated with interaction of an electronic excitation with its environment (e.g., disparate electronic excitations, vibrational or vibronic excitations . . . ) which leads to decay of the electronic excitation in disparate excitations (e.g., a collective plasmon excitation decays into a set of single-particle excitation).

At act 570, time-of-flight (TOF) energy analysis of photoemitted electrons is conducted to assess relaxation of the electronic excitation according to aspects described hereinbeofore. At act 580, an electronic population is generated associated with the electronic excitation. In an aspect, TOF energy analysis of act 570 facilitates, at least in part, generation of such a population via accumulation statistics of detected photoelectrons within an energy range.

Figure 6:
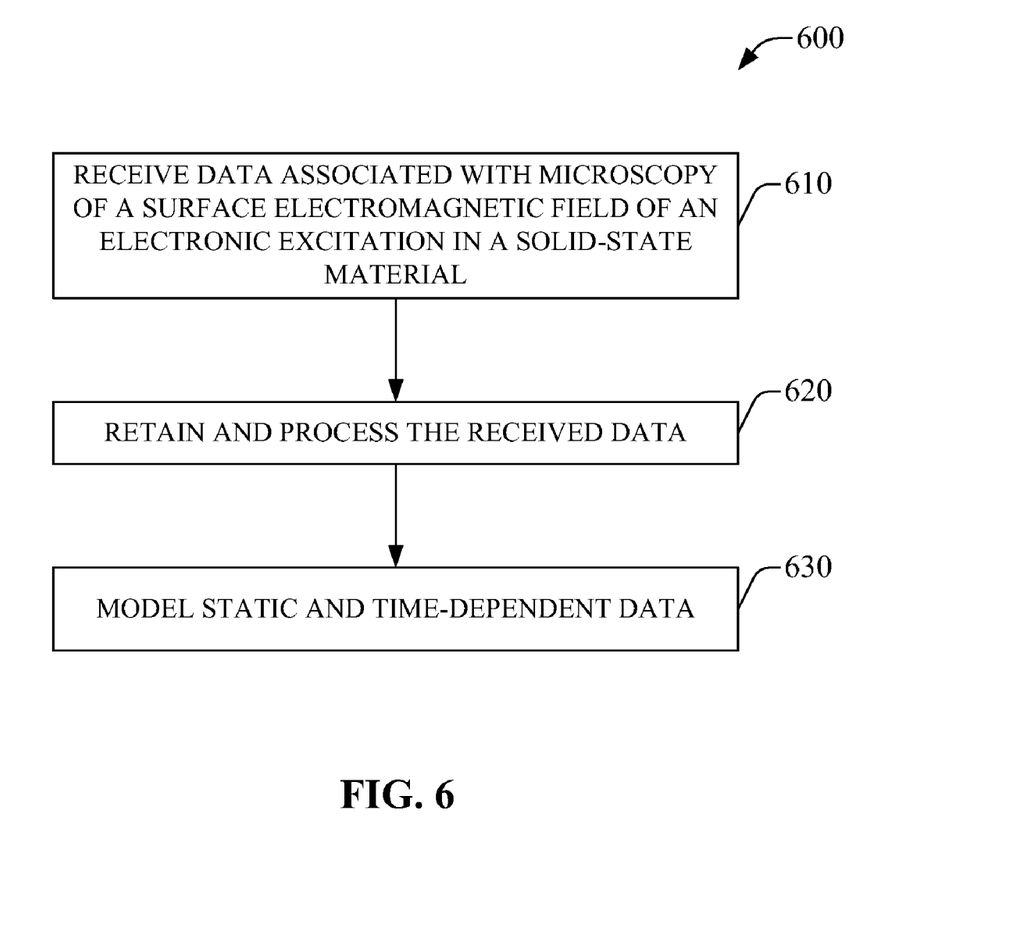
FIG. 6 is a flowchart of an example method for analyzing 4-dimensional spectroscopic data according to aspects described herein.

FIG. 6 is a flowchart of an example method 600 for analyzing 4-dimensional spectroscopic data according to aspects described herein. At act 610, data associated with microscopy of a surface electromagnetic field of an electronic excitation in a solid state material is received. The data can include at least one of space-resolved two-photon photoemission spectroscopy measurements; time-resolved interferometric two-photon photoemission spectroscopy (e.g., time-dependent interferometric two-pulse correlation), which can provide quantitative evolution of phase and amplitude of coherent polarization associated with an electronic excitation; or energy-resolved time of flight multichannel statistics. At act 620, the received data is retained and processed. In an aspect, the received data can be retained (e.g., in memory 145) as a four-dimensional array ((x,y) position in a surface, energy, and delay time). In an aspect, as part of the processing, movies can be generated, wherein the movies (i) display space-resolved images the show how an electron population at specific electronic excitation energy evolves in time, or (ii) display how the electron population varies as a function of energy at a specific delay time $\Delta\tau$. In another aspect, various visualization strategies can be pursued, presenting several two- or three-dimensional renditions (e.g., cross-sections, false-color maps . . . ) of the received four-dimensional data. At act 630, static and time-dependent data is modeled. In an aspect, for nanoscopic plasmonic devices, effective-mass theory models are generally adequate to model photoemission microscopy images. Quantitative agreement and simulation can be obtained by empirically adjusting bulk wave-vector-dependent complex dielectric constants for the metal utilized in the device. Generally, modeling spectroscopy data requires computation of polarization or electromagnetic field at the surface of a sample or device that is probed, such computations can include quantum mechanical effects.

Figure 7:
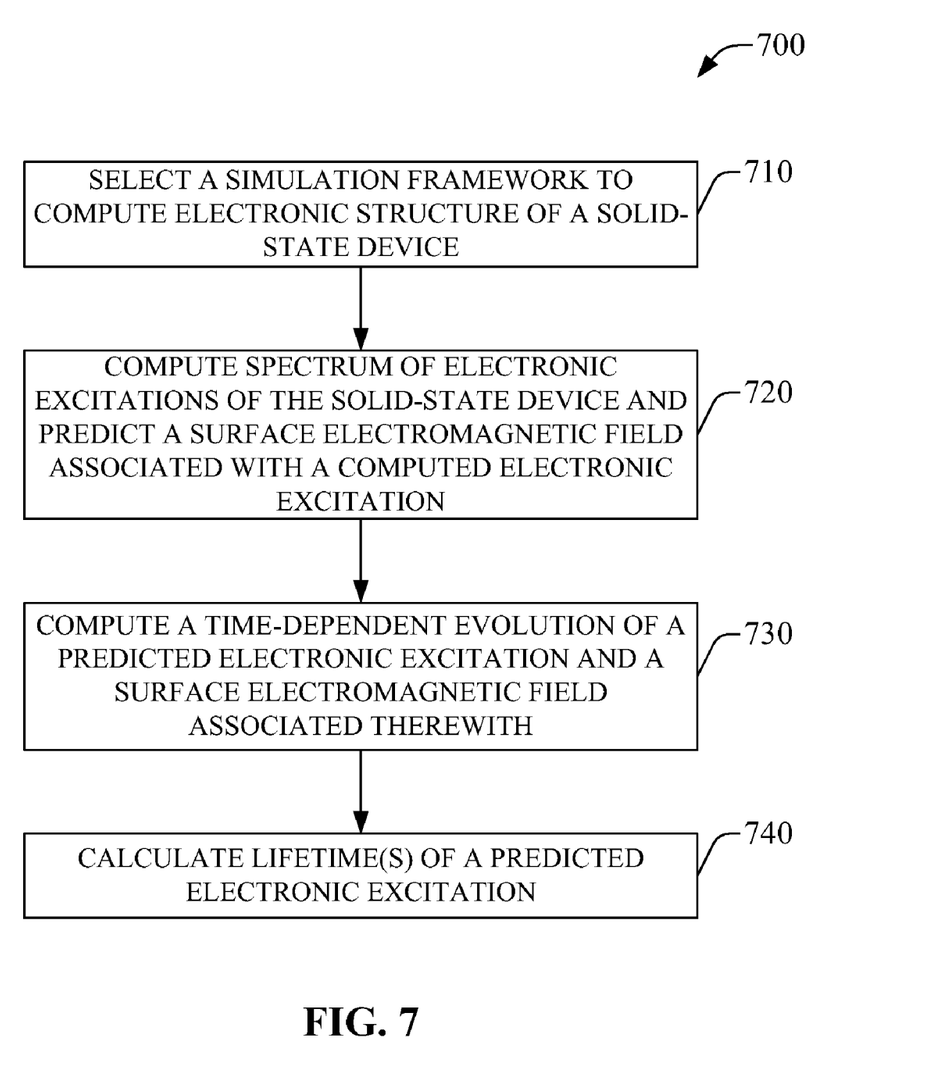
FIG. 7 presents a flowchart of an example method for modeling spectroscopic data of electromagnetic fields associated with electronic excitation in condensed matter gathered according to aspects described herein.

FIG. 7 presents a flowchart of an example method 700 for modeling spectroscopic data of electromagnetic fields associated with electronic excitation in condensed matter gathered according to aspects described herein. In an aspect, this example method 700 can be utilized in conjunction with example analysis method 600. At act 710, a simulation framework is selected to compute electronic structure of a solid state device. Available electronic structure provides energies that can be employed to select a light source for probing a sample or device through photoemission spectroscopy. Simulation frameworks can include effective mass theory, and empirical, semi-empirical and ab initio atomistic models (e.g., tight binding approach, pseudopotential approach, density functional theory). Simulation frameworks can be selected based at least in part on device complexity. At act 720, a spectrum of electronic excitations of the solid-state material is computed and a surface electromagnetic field associated with a computed electronic excitation is predicted. Computation of an electric field associated with electronic excitations can be computed from resulting electronic charge densities, or charge densities of majority and minority carriers in magnetic materials. Computation of electronic excitations is typically conducted within the same simulation framework selected for computing electronic structure. It should be appreciated that computation of electronic excitation spectrum provides a set of energies that can be utilized to select a light source for creation of predetermined excitation.

At act 730, an evolution (e.g., time-dependent behavior) of a predicted electromagnetic excitation and a surface electromagnetic field associated therewith is computed. In an aspect, the computation can be based on evolution of a wave-packet that describes the electronic excitation, the evolution can be based at least in part on propagation of a set of Fourier modes that make up the wave-packet. At act 740, lifetime(s) of a predicted electronic excitation are calculated. Such calculation typically exploits a computed electronic structure for the device, and available electronic excitation energies, in addition to coupling mechanisms (e.g., interaction Hamiltonian operators) that describe interaction of quasi-particles that make up the electronic excitation (e.g., plasmons, polaritons, excitons) with other quasi-particles (e.g., phonons, magnons, spins) or external perturbations or fields (e.g., magnetic field, electric field)

Figure 8:
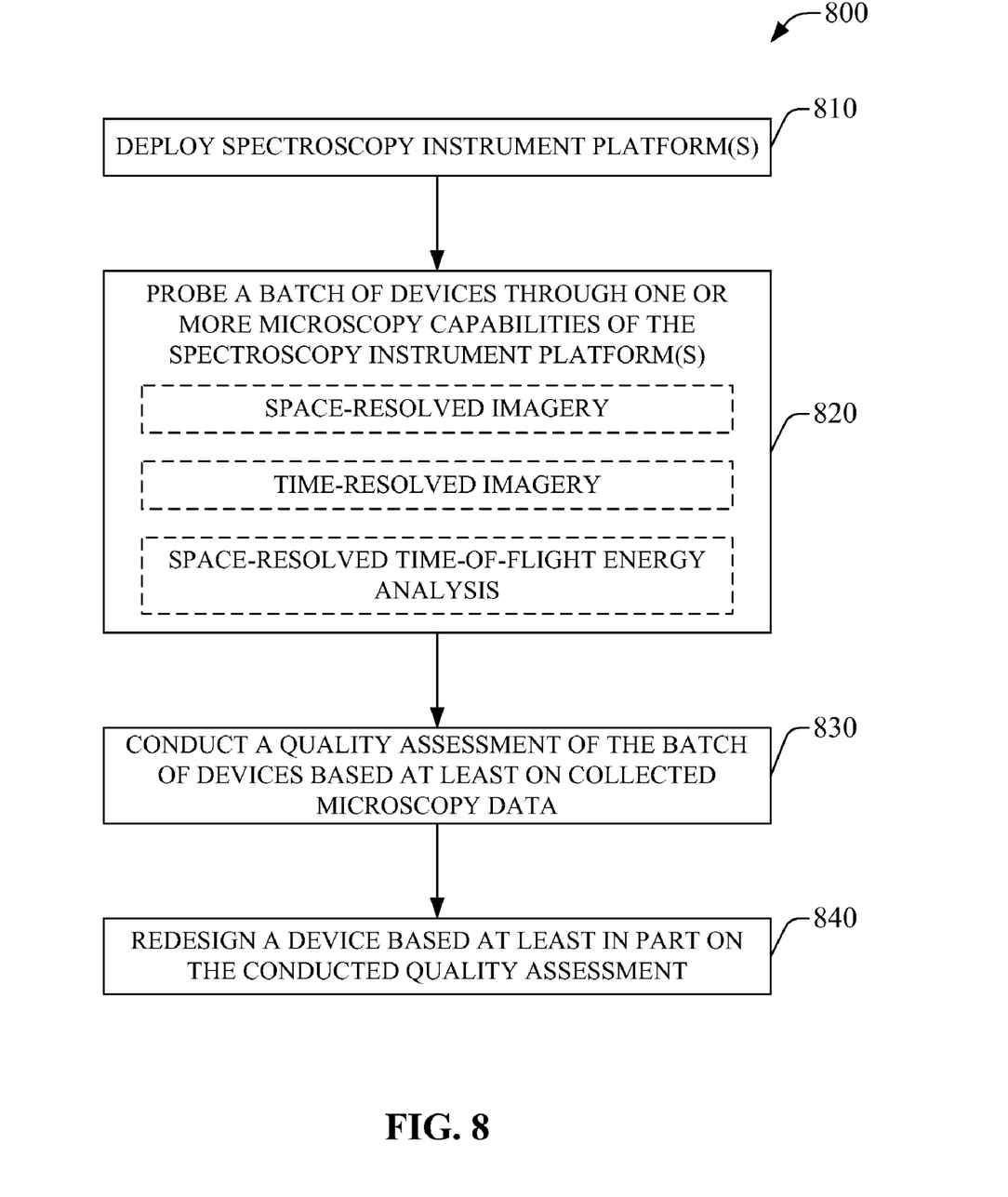
FIG. 8 is a flowchart of an example method for exploiting space-, time-, and energy-resolved microscopy for quality assurance of solid-state devices according to aspects described herein.

FIG. 8 is a flowchart of an example method 800 for exploiting space-, time-, and energy-resolved microscopy for quality assurance (QA) of solid-state devices. At act 810, microscopy instrument platform(s) are deployed. At act 820, a batch of devices is probed through one or more microscopy capabilities of the deployed microscopy instrument platform(s). Such QA experiments can be designed to assess specific aspects of functional integrity, e.g., uniformity of nanostructured features that provide functionality, presence of defects in operation critical areas of a device, dephasing times of specific electronic excitations, lifetime of specific electronic excitations, and so forth. Batch of devices can be sampled prior to conducting spectroscopy associated with QA analysis. At act 830, a quality assessment of the batch of devices based at least in part on collected microscopy data is conducted. In an aspect, statistics associated with extracted data is evaluated and contrasted with predetermined standards, failure to meet such standards can results in recommendations, e.g., to a specific research and development department, to revise processes associated with sample or device preparation; e.g., holographic lithography steps may need revision in view of highly non-uniform nanoscopic features (e.g., gratings, dielectric patterns) in devices. In another aspect, QA analysis can be directed to root cause analysis of failed devices on a testbed or in the field (e.g., an ultrafast plasmonic device).

Various aspects or features described herein may be implemented as a method, apparatus, or article of manufacture using standard programming and/or engineering techniques. In particular, the aspects or features can be implemented through program modules stored in a memory and executed by a processor, and/or other combination of hardware and software, e.g., firmware. The term "article of manufacture" as used herein is intended to encompass a computer program accessible from any computer-readable device, carrier, or media. For example, computer readable media can include but are not limited to magnetic storage devices (e.g. hard disk, floppy disk, magnetic strips . . . ), optical disks (e.g., compact disk (CD), digital versatile disk (DVD) . . . ), smart cards, and flash memory devices (e.g., card, stick, key drive . . . ).

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. A processor may also be implemented as a combination of computing processing units.

In the subject specification, terms such as "data store," "data storage," "database," and substantially any other information storage component relevant to operation and functionality of a component, refer to "memory components," or entities embodied in a "memory" or components comprising the memory. By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An instrument platform that facilitates probing an electronic excitation, the instrument platform comprising:
    an optical excitation component that generates a first laser pulse employed to generate the electronic excitation, and a second laser pulse utilized to probe the electronic excitation; and
    a microscopy component that comprises a photoemission electron microscope, a photoelectron spectrometer, a time-of-flight energy analysis component, an environmental control component and a human-machine interface, wherein the microscopy component collects data that characterizes the electronic excitation, and provides a space-resolved, time-resolved, and energy-resolved image of at least one of an electromagnetic field associated with the electronic excitation or an electronic population associated with the electronic excitation, and wherein the time-of-flight energy analysis component comprises a processor that conducts time-of-flight energy analysis of photoemitted electrons.

2. The instrument platform of claim 1, the microscopy component detects photoemitted electrons from a solid state device with a spatial resolution of no more than 50 nanometers.

3. The instrument platform of claim 2, further comprising a sample preparation component that prepares the solid state device, wherein the solid state device is prepared to be probed with the first or second laser pulse to extract the electromagnetic field associated with the excitation.

4. The instrument platform of claim 3, further comprising a modeling component that analyzes the collected data and creates a simulation based at least in part on the analysis.

5. The instrument platform of claim 1, the first laser pulse is generated through a Ti:sapphire laser oscillator and the second pulse laser is a coherently generated replica of the first pulse, the replica generated in a Mach-Zehnder interferometer.

6. The instrument platform of claim 5, the first and second laser pulses have durations of no more than 10 femtoseconds, and wavelengths that range from the ultra-violet to the infrared section of the electromagnetic radiation spectrum.

7. The instrument platform of claim 6, the first and second laser pulses exhibit a mutual delay that is defined with a resolution of no more than 50 attoseconds.

8. The instrument platform of claim 2, the solid state device includes a plurality of conducting and semiconducting materials, at least one of the materials displays nanometer scale features.

9. A method for mapping an electromagnetic field in a surface of a device, comprising:
    generating a first laser pulse;
    generating an electronic excitation in a material through the first laser pulse;
    generating a space-resolved image of an electromagnetic (EM) field associated with the electronic excitation;
    generating a second laser pulse that is delayed with respect to the first laser pulse;
    probing the electronic excitation with an electromagnetic field of the second laser pulse;
    scanning a delay between the first and second laser pulses, and recording an interference pattern between a probe electromagnetic field and the electromagnetic field associated with the electronic excitation to monitor dynamics of the electromagnetic field associated with the electronic excitation; and
    conducting time-of-flight energy analysis of photoemitted electrons to assess relaxation of the electronic excitation.

10. The method of claim 9, wherein conducting time-of-flight (TOF) energy analysis of photoemitted electrons to assess relaxation of the excitation includes detecting photoemitted electrons with a wired grid detector with spatial resolution and the TOF electron kinetic energy resolution.

11. The method of claim 10, the first and second laser pulses have time durations of no more than 10 femtoseconds, and wavelengths that range from the ultra-violet to the edge of the visible section of the electromagnetic radiation spectrum.

12. The method of claim 11, the first and second laser pulses are coherent and exhibit a mutual delay that is defined with a resolution of no more than 50 attoseconds.

13. The method of claim 12, the material is one of a metal, a semimetal, or a semiconductor, and displays nanometer scale features.

14. The method of claim 13, further comprising:
    probing a batch of devices by at least one of generating a space-resolved image of an electromagnetic field associated with an electronic excitation, scanning a delay between the first and second pulse lasers to monitor dynamics of an electromagnetic field associated with an electronic excitation, or conducting time of flight analysis of photoemitted electrons to determine a relaxation of an electronic excitation; and
    conducting a quality assessment of the batch of devices based at least in part on collected microscopic data.

15. The method of claim 14, further comprising redesigning a device based at least in part on the conducted quality assessment.

16. The method of claim 15, further comprising:

receiving static and time-dependent space-resolved and energy-resolved data associated with microscopy of a surface electromagnetic field of an electronic excitation in a solid-state material;

and modeling the received static and time dependent space-resolved and energy-resolved microscopy data.

17. The method of claim 16, wherein modeling static and time dependent space-resolved and energy-resolved microscopy data, includes:

selecting a simulation framework to compute electronic structure of a solid-state device with nanometer scale features;

computing spectrum of electronic excitations of the solid-state device, and predicting a surface electromagnetic field associated with a computed excitation;

computing an evolution of a predicted electronic excitation and a surface electromagnetic field associated therewith; and calculating lifetime(s) of a predicted electronic excitation.

* * * * *